United States Patent
Bailey

(10) Patent No.: US 9,788,632 B2
(45) Date of Patent: Oct. 17, 2017

(54) HAND-TOOL GRIPS

(71) Applicant: BAILEY INSTRUMENTS LIMITED, Manchester (GB)

(72) Inventor: Timothy Bailey, Manchester (GB)

(73) Assignee: Bailey Instruments Limited (GB)

( * ) Notice: Subject to any disclaimer, the term of this patent is extended or adjusted under 35 U.S.C. 154(b) by 199 days.

(21) Appl. No.: 14/441,704

(22) PCT Filed: Oct. 28, 2013

(86) PCT No.: PCT/GB2013/000458
§ 371 (c)(1),
(2) Date: May 8, 2015

(87) PCT Pub. No.: WO2014/072670
PCT Pub. Date: May 15, 2014

(65) Prior Publication Data
US 2015/0282586 A1    Oct. 8, 2015

(30) Foreign Application Priority Data
Nov. 10, 2012  (GB) .................................... 1220252.9

(51) Int. Cl.
| | |
|---|---|
| A45D 29/02 | (2006.01) |
| B25G 1/10 | (2006.01) |
| A61B 17/32 | (2006.01) |
| B25G 1/01 | (2006.01) |
| B26B 17/00 | (2006.01) |
| A61B 17/00 | (2006.01) |

(52) U.S. Cl.
CPC .............. *A45D 29/02* (2013.01); *A61B 17/32* (2013.01); *B25G 1/01* (2013.01); *B25G 1/105* (2013.01); *B26B 17/00* (2013.01); *A61B 2017/00424* (2013.01); *A61B 2017/00743* (2013.01)

(58) Field of Classification Search
CPC ...... A45D 29/02; B26B 17/00; B26B 17/003; B26B 17/006; B26B 17/02; B26B 21/40; B26B 21/52–21/528
USPC .............................. 30/28, 175–193, 229–262
See application file for complete search history.

(56) References Cited

U.S. PATENT DOCUMENTS

| | | | | |
|---|---|---|---|---|
| 3,398,451 | A | * 8/1968 | Angguist | ................ B26B 17/00 30/186 |
| 3,680,212 | A | * 8/1972 | Rozmus | ................... B25B 7/12 30/191 |

(Continued)

FOREIGN PATENT DOCUMENTS

| | | |
|---|---|---|
| DE | 9303249 | 7/1993 |
| DE | 202009015323 | 6/2010 |

(Continued)

OTHER PUBLICATIONS

United Kingdom Examination Report dated Jun. 13, 2016 for Application No. GB1220252.9.

*Primary Examiner* — Jason Daniel Prone
*Assistant Examiner* — Richard Crosby, Jr.
(74) *Attorney, Agent, or Firm* — Hartman Global IP Law; Gary M. Hartman; Domenica N.S. Hartman

(57) ABSTRACT

A hand tool having hinged nipping or cutting blades and handles that are squeezed to effect the cutting or nipping action, at least one of the handles being profiled in cross section to accept and retain a slide-on cushion.

10 Claims, 1 Drawing Sheet

(56) References Cited

U.S. PATENT DOCUMENTS

| | | | | |
|---|---|---|---|---|
| 4,198,749 A | * | 4/1980 | Nordin | B25B 7/123 30/122 |
| 4,785,536 A | * | 11/1988 | Freyman | B23D 51/16 30/124 |
| 4,918,815 A | * | 4/1990 | Juros | B26B 17/02 30/181 |
| 5,524,344 A | * | 6/1996 | Bazal | A45D 29/02 132/73 |
| D390,080 S | * | 2/1998 | Baldesberger | D8/57 |
| 5,862,597 A | * | 1/1999 | Juros | B26B 17/02 30/186 |
| 5,878,501 A | * | 3/1999 | Owens | B26B 5/00 30/286 |
| 5,941,892 A | * | 8/1999 | Cohn | A61B 17/3213 30/151 |
| D417,601 S | * | 12/1999 | Rivera | D8/107 |
| 6,131,244 A | | 10/2000 | Bares | |
| D436,514 S | * | 1/2001 | Rivera | D8/105 |
| 6,202,518 B1 | * | 3/2001 | Moffitt, Jr. | B25B 7/00 81/418 |
| D446,102 S | * | 8/2001 | Chen | D8/75 |
| 6,270,134 B1 | * | 8/2001 | Lin | B25B 7/00 16/422 |
| 6,752,054 B2 | * | 6/2004 | Knight | B26B 13/26 30/251 |
| 6,776,073 B1 | * | 8/2004 | Brady | B25B 7/00 81/416 |
| D506,115 S | * | 6/2005 | King | D8/54 |
| 6,966,244 B2 | * | 11/2005 | Herbst | B25B 7/02 30/186 |
| D533,307 S | * | 12/2006 | Ross | D28/60 |
| 7,730,811 B2 | * | 6/2010 | Robinson | B25B 7/00 81/415 |
| 8,096,053 B2 | * | 1/2012 | Wong | A45D 29/02 30/125 |
| 8,458,908 B2 | * | 6/2013 | Fischer | B26B 19/06 30/34.05 |
| 8,782,908 B2 | * | 7/2014 | Moffatt | B26D 5/16 30/251 |
| 9,257,806 B2 | * | 2/2016 | Lai | H01R 43/042 |
| 9,321,152 B2 | * | 4/2016 | Heinsohn | B25B 7/08 |
| 9,660,407 B2 | * | 5/2017 | Chou | H01R 43/042 |
| 2004/0000058 A1 | * | 1/2004 | Shyr | A01G 3/02 30/262 |
| 2005/0097998 A1 | * | 5/2005 | Herbst | B25B 7/02 81/418 |
| 2005/0160604 A1 | * | 7/2005 | Di Bitonto | A45D 29/02 30/28 |
| 2009/0078278 A1 | * | 3/2009 | Tran | A45D 29/02 132/75.5 |
| 2009/0308132 A1 | * | 12/2009 | Lai | B25B 27/146 72/409.16 |
| 2011/0061239 A1 | * | 3/2011 | Pacio | A45D 29/02 30/28 |
| 2012/0011723 A1 | * | 1/2012 | Flaten | A45D 29/02 30/28 |
| 2014/0224083 A1 | * | 8/2014 | Gupta | B25G 1/102 81/427.5 |
| 2016/0059427 A1 | * | 3/2016 | Stanley | A61B 17/8863 30/124 |

FOREIGN PATENT DOCUMENTS

| | | |
|---|---|---|
| GB | 2465329 | 5/2010 |
| JP | 2001334475 | 12/2001 |

* cited by examiner

HAND-TOOL GRIPS

BACKGROUND OF THE INVENTION

This invention relates to hand-tool grips, particularly, but not exclusively for nippers, especially podiatry nail nippers.

A problem with podiatrists' nail nippers is that they give rise to repetitive strain injury (RSI) when used perhaps hundreds of times a day by podiatrists.

This is especially true of multiple use nippers that are not especially sharp, the impact of the blades one against the other when the nail is penetrated being transmitted through the handles to the podiatrist's hand.

Similar problems arise also with mechanics' pliers and snips.

It is a problem to provide cushioning for the handles that is adequate to cushion the impact yet is easy and inexpensive to attach to the handles. Often, a sleeve is applied which is profiled to fit the handle, sometimes cushioning is glued in place. These problems arise especially in the case of instruments that need to be sterilised, as the sterilisation process can affect adhesives. It is also desirable, in the case of single-use, disposable instruments, that the cost be kept to a minimum.

BRIEF DESCRIPTION OF THE INVENTION

The present invention provides hand tools such as podiatry nippers that have improved handle provision.

The invention comprises a hand tool comprising hinged nipping or cutting blades and handles that are squeezed to effect the cutting or nipping action, at least one of the handles being profiled in cross section to accept and retain a slide-on cushion.

The handle may be bifurcated and the cushion have an 'H' shaped cross section.

The cushion may have an end-stop that abuts the end of the handle remote from the blades.

The handle may be recessed from the hinge end by the thickness of the cushion to give a smooth transition at the hinge end of the cushion.

The hand tool may comprise an internal spring.

The blades of podiatrists' nippers may be razor sharp, and may have a flat cut. Razor sharpness may be a feature of disposable, single use, or at least limited use nail nippers, and further reduces the incidence of RSI as less force is required to cut through a nail than with multiple use nippers, which are manufactured less than razor sharp in order that they maintain a constant sharpness throughout their life. Razor sharp nippers dull quickly, but this is, of course, of no consequence in a disposable implement.

Nail nippers may be enclosed in a sterile pack, and may be sterilised by gamma radiation. The pack may contain other podiatry equipment such as a file, scissors, a scalpel and an emery board.

BRIEF DESCRIPTION OF THE DRAWINGS

A hand tool according to the invention will now be described with reference to the accompanying drawings, in which.

DETAILED DESCRIPTION OF THE INVENTION

The drawings illustrate a hand tool, in particular, a podiatrists' nipper 11, comprising hinged nipping or cutting blades 12 and handles 13 that are squeezed to effect the cutting or nipping action. The handles 13 are profiled in cross section to accept and retain a slide-on cushion 14, of which only one is shown, the other being a mirror image. Of course, both cushions could be the same, simplifying production.

Figure 1:
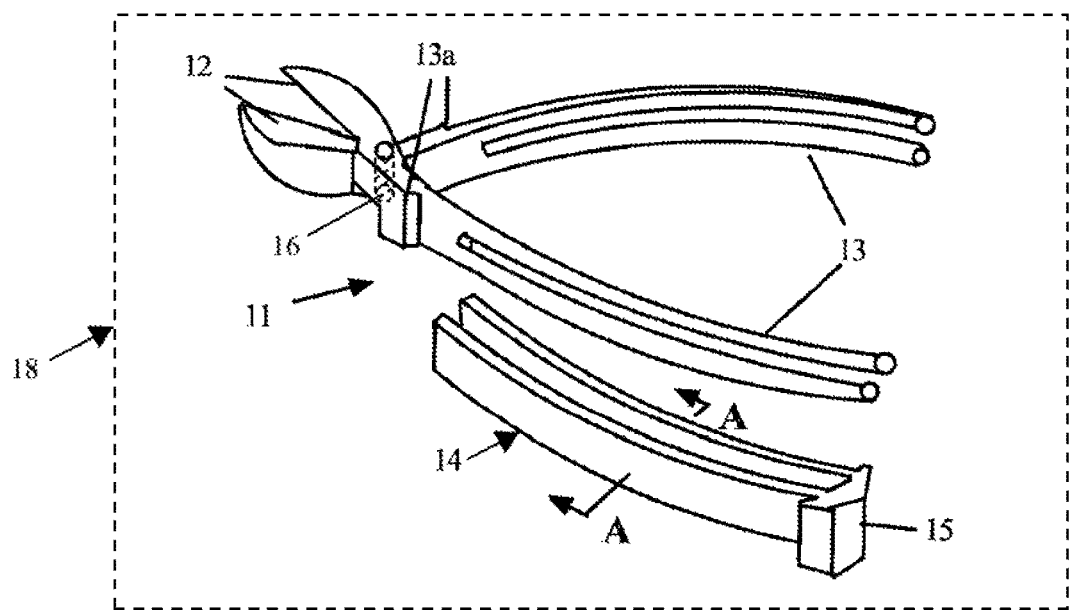
FIG. 1 is a view of a podiatrists' nail nipper and a slide on cushion.
Figure 2:
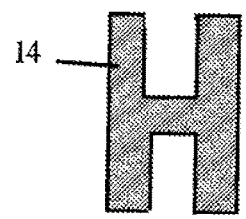
FIG. 2 is a cross-section of the cushion of FIG. 1 on the line A-A of that Figure.

The handles 13 are bifurcated and the cushion 14 has an 'H' shaped cross section as seen in FIG. 2.

The cushion 14 has an end-stop 15 that abuts the end of the handle 13 remote from the blades 12.

The handles 13 are recessed at 13a from the hinge end by the thickness of the cushion 14 to give a smooth transition at the hinge end of the cushion 14.

The tool 11 has an internal spring 16. This adapts the implement better to cleaning and sterilising, as there is essentially no trap for foreign matter. The tool 11 may be enclosed in a sterile pack 18.

The blade 12 are razor sharp, and have a flat cut, which is to say that they come together along their entire edged when closed, rather than just meeting at their ends. Razor sharpness is a feature particularly appropriate to disposable, single use, or at least limited use nail nippers, and further reduces the incidence of RSI as less force is required to cut through a nail than with multiple use nippers, which are manufactured less than razor sharp in order that they maintain a constant sharpness throughout their life. Razor sharp nippers dull quickly, but this is, of course, of no consequence in a disposable implement.

The cushions are made of an autoclavable polymer such as ethylene-vinyl acetate.

The invention claimed is:

1. A hand tool comprising hinged nipping or cutting blades, at least a first slide-on cushion, and handles adapted to be squeezed to effect a cutting or nipping action, at least one of the handles being profiled in cross section to accept and retain the first slide-on cushion, wherein the at least one handle is bifurcated to include a pair of elongated members and the first slide-on cushion has an 'H' shaped cross section having a pair of outer members connected with a cross member, wherein the at least one handle is configured to releasably accept and retain the first slide-on cushion by sliding the cross member between the pair of elongated members such that each of the pair of elongated members is located between the pair of outer members and the pair of elongated members are separated by the cross member.

2. A hand tool according to claim 1, wherein the first slide-on cushion has an end-stop that abuts the end of the handle remote from the blades.

3. A hand tool according to claim 2, further comprising an internal spring.

4. A hand tool according to claim 1, wherein the hand tool is a podiatrists' nippers.

5. A hand tool according to claim 4, wherein the blades are razor sharp.

6. A hand tool according to claim 4, wherein the blades have a flat cut.

7. A hand tool according to claim 1, wherein the first slide-on cushion is of autoclavable material.

8. A hand tool according to claim 7, wherein first slide-on cushion is of ethylene-vinyl acetate.

9. A hand tool according to claim 1, wherein the hand tool is enclosed in a sterile pack.

10. A hand tool according to claim 1, further comprising a second slide-on cushion, wherein each of the handles is profiled in cross section to accept and retain the first or second slide-on cushion.

\* \* \* \* \*